(12) United States Patent
Knieriem et al.

(10) Patent No.: US 9,861,104 B2
(45) Date of Patent: *Jan. 9, 2018

(54) METHOD FOR PRODUCING AN AQUEOUS SUSPENSION CONCENTRATE FORMULATION OF A PYRIPYROPENE INSECTICIDE

(71) Applicant: BASF SE, Ludwigshafen (DE)

(72) Inventors: Torsten Knieriem, Mannheim (DE); Tiziana Chiodo, Mannheim (DE); Christopher Koradin, Ludwigshafen (DE); Tanja Weber, Limburgerhof (DE); Walter Weishaar, Gruenstadt (DE)

(73) Assignee: BASF SE, Ludwigshafen (DE)

( * ) Notice: Subject to any disclaimer, the term of this patent is extended or adjusted under 35 U.S.C. 154(b) by 294 days.

This patent is subject to a terminal disclaimer.

(21) Appl. No.: 14/383,731

(22) PCT Filed: Mar. 11, 2013

(86) PCT No.: PCT/EP2013/054828
§ 371 (c)(1),
(2) Date: Sep. 8, 2014

(87) PCT Pub. No.: WO2013/135606
PCT Pub. Date: Sep. 19, 2013

(65) Prior Publication Data
US 2015/0018207 A1      Jan. 15, 2015

Related U.S. Application Data

(60) Provisional application No. 61/609,428, filed on Mar. 12, 2012.

(51) Int. Cl.
| | | |
|---|---|---|
| A01N 53/00 | (2006.01) | |
| A01N 25/08 | (2006.01) | |
| A01N 43/90 | (2006.01) | |

(52) U.S. Cl.
CPC .............. *A01N 53/00* (2013.01); *A01N 25/08* (2013.01); *A01N 43/90* (2013.01)

(58) Field of Classification Search
None
See application file for complete search history.

(56) References Cited

U.S. PATENT DOCUMENTS

| | | | |
|---|---|---|---|
| 3,948,636 A | 4/1976 | Marks | |
| 5,089,259 A | 2/1992 | Wessling et al. | |
| 5,807,721 A | 9/1998 | Omura et al. | |
| 7,241,454 B2 | 7/2007 | Warrington et al. | |
| 7,268,259 B1 | 9/2007 | Behler et al. | |

(Continued)

FOREIGN PATENT DOCUMENTS

| | | |
|---|---|---|
| CA | 2 609 527 | 12/2006 |
| EP | 2 107 060 | 10/2009 |

(Continued)

OTHER PUBLICATIONS

Office Action dated Sep. 8, 2016 in U.S. Appl. No. 134/383,665.

(Continued)

*Primary Examiner* — Abigail Vanhorn
*Assistant Examiner* — Erin Hirt
(74) *Attorney, Agent, or Firm* — Brinks Gilson & Lione

(57) ABSTRACT

The present invention relates to a method for producing an aqueous suspension concentrate formulation and novel suspension concentrate formulations of the compound of formula I.

Formula I

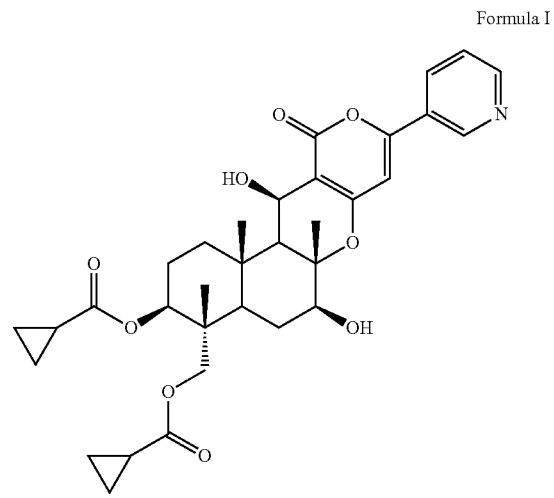

Figure 1:
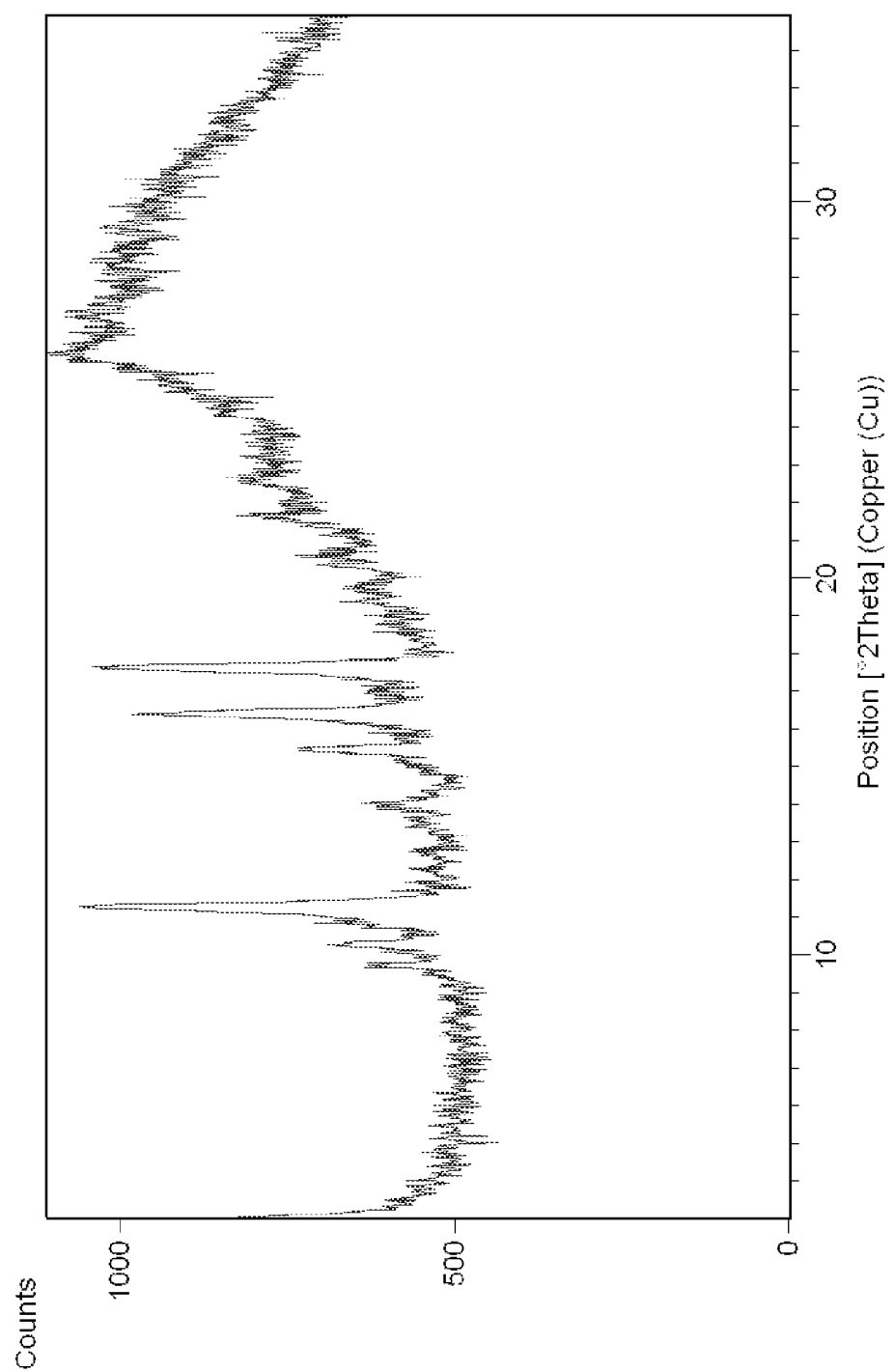

The method comprises:

a) providing an aqueous slurry of coarse particles of the compound of the formula I, where the compound of the formula I is at least partially present in its crystalline form B, which, in an X-ray powder diffractogram at 25° C. and Cu-K$_\alpha$ radiation, shows at least three, preferably at least four, in particular at least 5 or at least 7 or at least 9 or all of the following reflexes, given as 2θ values: 8.0±0.2°, 9.5±0.2°, 10.7±0.2°, 11.0±0.2°, 11.2±0.2°, 11.7±0.2°, 14.2±0.2°, 15.6±0.2°, 16.5±0.2°, 17.7±0.2°, 21.5±0.2°;

b) comminuting the coarse particles in the slurry of the compound of formula I, which is at least partially present in its form B, in the presence of the at least one surfactant.

32 Claims, 2 Drawing Sheets

(56) References Cited

U.S. PATENT DOCUMENTS

| | | |
|---|---|---|
| 7,491,738 B2 | 2/2009 | Goto et al. |
| 2004/0157743 A1 | 8/2004 | Rosenfeldt et al. |
| 2006/0165748 A1 | 7/2006 | Arimoto |
| 2008/0096763 A1 | 4/2008 | Dawson et al. |
| 2008/0300313 A1 | 12/2008 | Byrne et al. |
| 2008/0312290 A1 | 12/2008 | Vermeer et al. |
| 2009/0286877 A1 | 11/2009 | Arimoto et al. |
| 2010/0281584 A1 | 11/2010 | Horikoshi et al. |
| 2012/0046470 A1* | 2/2012 | Fukuda .............. C07D 493/04 546/283.1 |
| 2013/0184153 A1 | 7/2013 | Dieleman et al. |
| 2014/0142289 A1 | 5/2014 | Anzai et al. |
| 2014/0371178 A1 | 12/2014 | Horikoshi et al. |

FOREIGN PATENT DOCUMENTS

| | | | |
|---|---|---|---|
| EP | 2 186 815 | 5/2010 | |
| EP | 2 223 599 | 9/2010 | |
| EP | 1 889 540 | 11/2011 | |
| EP | 2 119 361 | 10/2013 | |
| JP | 2993767 | 10/1999 | |
| JP | 2002-522400 | 7/2002 | |
| JP | 2002-532464 | 10/2002 | |
| WO | WO 94/09147 | 4/1994 | |
| WO | WO 94/09417 | 4/1994 | |
| WO | WO 98/35553 | 8/1998 | |
| WO | WO 00/07709 | 2/2000 | |
| WO | WO 00/35863 | 6/2000 | |
| WO | WO 2004/060065 | 7/2004 | |
| WO | WO 2006/129714 | 12/2006 | |
| WO | WO 2007117001 | 10/2007 | |
| WO | WO 2008/013336 | 1/2008 | |
| WO | WO 2008/108491 | 9/2008 | |
| WO | WO 2009/081851 | 7/2009 | |
| WO | WO 2010010955 | 1/2010 | |
| WO | WO 2010129345 A2 * | 11/2010 | ............ A01N 25/04 |
| WO | WO 2011/113052 | 9/2011 | |
| WO | WO 2011/147952 | 12/2011 | |
| WO | WO 2011/147953 | 12/2011 | |
| WO | WO 2012/035015 | 3/2012 | |
| WO | WO 2013/135604 | 9/2013 | |
| WO | WO 2013/135605 | 9/2013 | |
| WO | WO 2013/135610 | 9/2013 | |

OTHER PUBLICATIONS

Office Action dated Sep. 30, 2014 in U.S. Appl. No. 13/822,514.
Office Action dated Oct. 1, 2014 in U.S. Appl. No. 13/822,530.
Final Office Action dated Apr. 2, 2015 in U.S. Appl. No. 13/822,514.
Office Action dated Apr. 20, 2015 in U.S. Appl. No. 13/822,530.
Office Action dated Jul. 13, 2015 in U.S. Appl. No. 14/383,661.
Narayanan, K.S., et al. "Macro and Microemulsion technology and trands", Pesticide Formulation and Adjuvant Technology, Foy, C.L. and Pritchard, D.W., CRC Press, Boca Raton, FL, 1996, p. 148-164.
Sunazuka, Toshiaki, et al., "Synthetic Study of α-Pyrone Meroterpenoids, Pyripyropens", Journal of Society of Synthetic Organic Chemistry, 1998, pp. 478-488, vol. 56, No. 6.
Omura, Satoshi, et al., "Pyripyropense, highly potent inhibitors of Acyl-CoA: Cholesterol Acyltransferase produced by *Aspergillus fumigatus*", Journal of Antibiotics, 1993, p. 1168-9, vol. 46, No. 7.
Wang, Hui-Juan, et al., Aflavinines and Other Antiinsectan Metabolites from the Ascostromata of *Eupenicillium crustaceum* and related Species, Applied and Environmental Microbiology, 1995, p. 4429-35, vol. 61, No. 12.
Wang, C.J., et al. "Foliar uptake of pesticides—present status and future challenge", Pesticide Biochemistry and Physiology, 2007, p. 1-8, vol. 87.
International Search Report dated Jun. 10, 2013 prepared in International Application No. PCT/EP2013/054828.
International Preliminary Report on Patentability dated Sep. 16, 2014 prepared in International Application No. PCT/EP2013/054828.
Office Action dated Mar. 14, 2017 from U.S. Appl. No. 14/383,665, filed Sep. 8, 2014.
Office Action dated Mar. 31, 2017 from U.S. Appl. No. 14/383,756, filed Sep. 8, 2014.
Office Action dated Jun. 8, 2017 from U.S. Appl. No. 13/822,514, filed Mar. 12, 2013.

* cited by examiner

METHOD FOR PRODUCING AN AQUEOUS SUSPENSION CONCENTRATE FORMULATION OF A PYRIPYROPENE INSECTICIDE

This application is a National Stage application of International Application No. PCT/EP2013/054828, filed Mar. 11, 2013, which claims the benefit of U.S. Provisional Application No. 61/609,428, filed Mar. 12, 2012, the entire contents of which are hereby incorporated herein by reference.

The present invention relates to a method for producing an aqueous suspension concentrate formulation and novel suspension concentrate formulations of the compound of formula I.

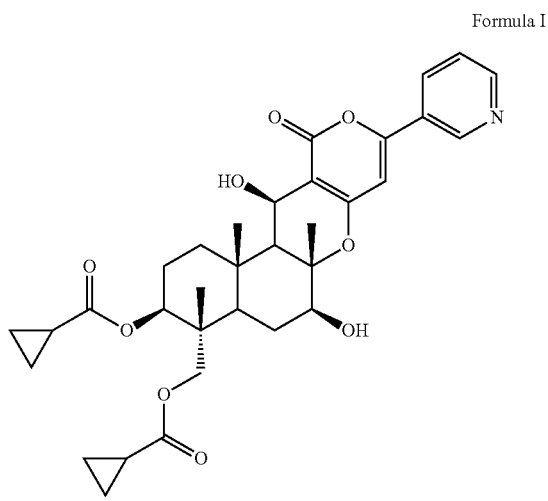

Formula I

The compound of formula I, hereinafter also termed pyripyropene derivative I, is known from EP 2223599 (compound no. 4) as exhibiting pesticidal activity against invertebrate pests, in particular against insects, and thus being useful for crop protection.

It is highly desirable to formulate a solid agriculturally active ingredient, such as a fungicide, herbicide or insecticide compound, as an aqueous suspension concentrate formulation, as these formulations contain no or only small amounts of organic volatiles. On the other hand, suspension concentrate formulations of solid organic active ingredients tend to be unstable against settling of the active ingredient due to particle growth or agglomeration of the active compound particles. Aqueous suspension concentrates are liquid aqueous formulations, which contain the active ingredient in the form of a suspension of particles suspended in the aqueous phase of the formulation. Aqueous suspension concentrates are usually prepared by suspending the solid active ingredient in an aqueous liquid containing a suitable surfactant for stabilizing the solid particles of the active ingredient and then comminuting the active ingredient particles down to the desired particle size, which is normally below 10 µm (volume average diameter as determined by light scattering).

EP 2223599 suggests various agrochemical formulations of the pyripyropene derivative I, including an aqueous suspension concentrate formulation, and suitable additives for such formulations. However, when trying to formulate the pyripyropene derivative I as an aqueous suspension concentrate, one faces several difficulties, as the formulation has only poor stability upon storage. In particular pronounced particle growth is observed, presumably due to the formation of agglomerates. Moreover, it is difficult to prepare an aqueous suspension concentrate of pyripyropene derivative I, as gelling may occur upon comminuting the active ingredient particles.

Earlier filed International Patent Application WO 2012/035015 shows that different hydrates forms of pyripyropene derivative I and hydrate formation may be one reason for the inherent instability of the aqueous suspension concentrate formulations of EP 2223599. WO 2012/035015 teaches that the stability problems can be overcome by providing a suspension concentrate formulation of the pyripyropene derivative I, which contains specific surfactant combination, i.e.

6 to 20 wt %, based on the total weight of the formulation, of an anionic polymeric surfactant having a plurality of $SO^{3-}$ groups, and 0.1 to 10 wt %, based on the total weight of the formulation, of a non-ionic surfactant, in particular a poly(ethyleneoxide-co-propyleneoxide) polymers having a HLB of at least 12.

It is believed that the specific surfactant system of WO 2012/035015 favours the formation of a specific hydrate form, namely form Y (also termed form A), which renders the formulation more stable. Form Y in an X-ray powder diffractogram at 25° C. and Cu-K$_\alpha$ radiation, shows at least three, frequently at least four, in particular at least 5 or all of the following reflexes, given as 2θ values: 9.7±0.2°, 10.3±0.2°, 11.3±0.2°, 14.0±0.2°, 15.5±0.2°, 16.4±0.2°, 17.6±0.2°. Nevertheless, the problem of gelling occurs, in particular, if the compound of formula I has a purity of 95% or higher, especially a purity of 97% or higher.

The inventors of the present invention found that the problems associated with the formulation of pyripyropene derivative I as an aqueous suspension concentrate can be overcome by a specific method of its preparation, which method includes providing an aqueous slurry of coarse particles of the pyripyropene derivative I, wherein the pyripyropene derivative I is at least partially present in its crystalline form B described in WO 2012/035015. Form B, in an X-ray powder diffractogram at 25° C. and Cu-K$_\alpha$ radiation, shows at least three, preferably at least four, in particular at least 5 or at least 7 or at least 9 or all of the following reflexes, given as 2θ values: 8.0±0.2°, 9.5±0.2°, 10.7±0.2°, 11.0±0.2°, 11.2±0.2°, 11.7±0.2°, 14.2±0.2°, 15.6±0.2°, 16.5±0.2°, 17.7±0.2°, 21.5±0.2°.

Therefore, the present invention in a first aspect relates to a method for producing an aqueous suspension concentrate formulation of a compound of formula I, which formulation contains the compound of formula I in the form of fine particles and which also contains at least one surfactant and water, which method comprises:

a) providing an aqueous slurry of coarse particles of the compound of the formula I, where the compound of the formula I is at least partially present in its crystalline form B, which, in an X-ray powder diffractogram at 25° C. and Cu-K$_\alpha$ radiation, shows at least three, preferably at least four, in particular at least 5 or at least 7 or at least 9 or all of the following reflexes, given as 2θ values: 8.0±0.2°, 9.5±0.2°, 10.7±0.2°, 11.0±0.2°, 11.2±0.2°, 11.7±0.2°, 14.2±0.2°, 15.6±0.2°, 16.5±0.2°, 17.7±0.2°, 21.5±0.2°;

b) comminuting the coarse particles in the slurry of the compound of formula I, which is at least partially present in its form B, in the presence of the at least one surfactant.

Upon comminuting the coarse particles of form B in the aqueous slurry of the pyripyropene derivative I in the presence of the at least one surfactant, down to the desired particle size, the pyripyropene derivative I is at least partially, generally to an extent of at least 50%, in particularly to at least 80%, and especially completely or almost completely, i.e. to at least 90%, converted into its form Y as described above. The at least partial conversion into form Y imparts particular stability to the aqueous suspension concentrate formulation.

Different from the findings in WO 2012/035015, there is no particular need to use a specific surfactant combination to achieve the conversion of pyripyropene derivative I into its form Y, as long as at least a portion, generally at least 50 wt %, in particular at least 70 wt %, especially at least 80 wt % or the total amount of the pyripyropene derivative I contained in the slurry prior to comminution is present in its form B. Thus, the process of the invention allows to choose other surfactants or surfactant combinations than those of WO 2012/035015. However, the specific surfactant combination of WO 2012/035015 favours the formation of form Y.

Therefore, the invention also relates to an aqueous suspension concentrate formulation of the pyripyropene derivative I, i.e. a formulation, where the compound of formula I is present in the form of finely dispersed particles, wherein the compound of the formula I is at least partially present in its form Y which, in an X-ray powder diffractogram at 25° C. and Cu-K$_\alpha$ radiation, shows at least three, frequently at least four, in particular at least 5 or all of the following reflexes, given as 2θ values: 9.7±0.2°, 10.3±0.2°, 11.3±0.2°, 14.0±0.2°, 15.5±0.2°, 16.4±0.2°, 17.6±0.2°.

The present invention relates in particular to an aqueous suspension concentrate formulation of the pyripyropene derivative I, i.e. a formulation, where the compound of formula I is present in the form of finely dispersed particles, wherein the compound of the formula I is at least partially present in its form Y which, in an X-ray powder diffractogram at 25° C. and Cu-K$_\alpha$ radiation, shows at least three, frequently at least four, in particular at least 5 or all of the following reflexes, given as 2θ values: 9.7±0.2°, 10.3±0.2°, 11.3±0.2°, 14.0±0.2°, 15.5±0.2°, 16.4±0.2°, 17.6±0.2°. except for the suspension concentrate formulations of WO 2012/035015, i.e. except for a formulation containing from 6 to 20 wt %, based on the total weight of the formulation, of at least one anionic polymeric surfactant having a plurality of $SO_3^-$ groups.

In this context, the phrase "at least partially present in its form B" means that the pyripyropene derivative I is present in its form B to an extent of generally at least 50 wt %, in particular at least 70 wt %, especially at least 80 wt %, completely or almost completely (i.e. at least 90 wt %), based on the total amount of the pyripyropene derivative I.

In this context, the phrase "at least partially present in its form Y" means that the pyripyropene derivative I is present in its form Y to an extent of generally at least 50 wt %, in particular at least 70 wt %, especially at least 80 wt %, completely or almost completely (i.e. at least 90 wt %), based on the total amount of the pyripyropene derivative I.

The expression "wt %" as used herein means "% by weight".

In the first step of the method of the present invention, an aqueous slurry of coarse particles of the compound of the formula I is provided, where the compound of the formula I is at least partially, i.e. to an extent of generally at least 50 wt %, in particular at least 70 wt %, especially at least 80 wt %, completely or almost completely (i.e. at least 90 wt %), present in its crystalline form B.

The term "coarse particle" means that the particles are bigger than the particles usually contained in a suspension concentrate formulation, which means that the volume average diameter of the particles of pyripyropene derivative I generally exceeds 10 µm, and is in particular at least 15 µm or at least 20 µm and may range from 10 µm to 1000 µm, in particular from 15 µm to 500 µm or from 20 µm to 200 µm.

The average particle diameter, as referred herein, is the volume average particle diameter d(0.5) or d(v, 0.5), respectively, i.e. 50 vol.-% of the particles have a diameter which is above the value cited and 50 vol.-% of the particles have a diameter which is below the value cited. Therefore, average particle diameters are also termed "volume median diameters". Such average particle diameters can be determined by dynamic light scattering (usually performed on diluted suspensions containing from 0.01 to 5% by weight of the active ingredient). A skilled person is familiar with these methods which are described e.g. in H. Wiese (D. Distler, Ed.), Aqueous Polymer Dispersions (Wässrige Polymerdispersionen), Wiley-VCH 1999, Chapter 4.2.1, p. 40ff, and the literature cited therein; H. Auweter, D. Horn, J. Colloid Interf. Sci. 105 (1985), p. 399; D. Lilge, D. Horn, Colloid Polym. Sci. 269 (1991), p. 704; and H. Wiese, D. Horn, J. Chem. Phys. 94 (1991), p. 6429.

The slurry, where the compound of the formula I is at least partially present in its crystalline form B can be simply provided by suspending the form B in water, which may or may not contain at least a portion of the surfactant.

The crystalline form B and methods for preparing form B have been described in WO 2012/035015 to which full reference is made. Form B is a non-stoichiometric hydrate of the compound of formula I. The typical water content is in the range from 7.5 to 9 wt % and in particular about 8.5 wt %, i.e. 8.5±0.2 wt %. The water content can be determined by thermogravimetric analysis (TGA) or by Karl Fischer titration. In a TGA measurement form B shows desolvation at a temperature in the range from 65 to 70° C., in particular in the range from 66 to 68° C. Desolvation results in the amorphous compound of formula I. Form B is stable at room temperature in the presence of mother liquor or water but slowly converts into an other hydrate form C, when the mother liquor is removed or into amorphous material, if form B is dried.

Form B can be prepared by conventional crystallization techniques, e.g. by crystallization from a water containing organic solvent, in particular a water containing organic solvent, which is at least partially miscible with water (miscibility at least 20 wt % at 25° C.) or preferably completely miscible with water (at 25° C.). Suitable organic solvents are $C_1$-$C_4$ alkanols, such as ethanol or isopropanol, acetone, dimethyl sulfoxide, acetonitrile or cyclic ethers such as tetrahydrofurane. For obtaining form B by conventional crystallization, the water content in the water containing organic solvent is from 20 to 90 wt %. Conventional techniques include evaporation crystallization or precipitation crystallization. For precipitation crystallization or evaporation crystallization, the compound of formula I is dissolved in the water containing aqueous organic solvent or in dry organic solvent, followed by the addition of water. Crystallization can be effected by cooling or by addition of further water to reduce solubility of the compound of formula I in the water containing organic solvent. Alternatively, crystallization can be effected by removing solvent, e.g. by evaporation. Addition of seed crystals of form B will help to achieve quantitative conversion of the compound I into form B. Preferably, precipitation crystallization or evaporation crystallization is performed at temperatures in the range from 0 to 60° C., in particular from 5 to 50° C. Form B can also be prepared by slurry crystallization, which comprises providing a slurry of the compound of formula I in water or in the water containing organic solvent. Thereby, the solid compound of formula I converts into form B. For the purpose of slurry crystallization, aqueous organic solvents or water can be used. The amount of water in the solvent used for slurry crystallization may range from 10 to 100 wt %. Suitable organic solvents are $C_1$-$C_4$ alkanols, such as ethanol or isopropanol, ethylene glycol, glycerol, acetone, dimethyl sulfoxide, acetonitrile or cyclic ethers such as tetrahydrofurane. Preferably, slurry crystallization is performed at temperatures in the range from 0 to 60° C., in particular from 5 to 50° C. The time required for conversion into form B may range from 1 h to 10 d, depending on the temperature and the solvent. Addition of seed crystals of form B will help to achieve quantitative conversion of the compound I into form B.

As a starting material for the preparation of form B, any crystalline or amorphous form of the pyripyropene derivative I can be used, which is different from forms B and Y.

In a preferred embodiment of the invention, the form B is prepared in situ from a form of the pyripyropene derivative I, which is different from forms B and Y. Preparation in situ is understood that an aqueous slurry of the compound of formula I in a solid form different from form B is provided, and then the compound of formula I is converted into its form B in the aqueous slurry. The solid form which is used for in situ preparation may be an amorphous form, an anhydrate form or a solvate form with an organic solvate, or a hydrate form which is different from forms B and Y. The solid compound of the formula I which is used in the preparation of the suspension of step b) may be amorphous, crystalline or semicrystalline and is employed in particulate form, e.g. as a powder, as crystals, as a granulate or as a comminuted solidified melt. The particles of the solid active compound may be of regular or irregular shape, e.g. of spherical or virtually spherical form or in the form of needles.

In situ preparation of form B is generally achieved by suspending the solid form of the compound of formula I, which is different from form B and preferably also different from form Y, in water to obtain an aqueous slurry of coarse particles of the compound of formula I and keeping the aqueous slurry of coarse particles of the compound of formula I for a time sufficient to achieve at least partial conversion of the compound of formula I into its form B.

The surfactant which must be present during comminution in step b) may be present in the water, wherein the solid form of the pyripyropene derivative I is suspended, or it is added to the slurry at any time prior to step b).

Therefore a particular embodiment of the method of the invention comprises the following steps:
a1) suspending a solid form of the compound of formula I, which is different from form B and preferably also different from form Y, in water to obtain an aqueous slurry of coarse particles of the compound of formula I;
a2) keeping the aqueous slurry of coarse particles of the compound of formula I for a time sufficient to achieve at least partial conversion of the compound of formula I into its form B;
a3) addition of at least one surfactant during steps a1) or a2) or after step a2).
b) comminuting the coarse particles in the slurry of the compound of formula I, which is at least partially present in its form B, after the addition of the at least one surfactant.

For the conversion of the coarse particles of the pyripyropene derivative I into coarse particles comprising form B it is generally preferred that the volume average particle size of the coarse particles does not exceed 1000 μm, in particular not exceed 500 μm, especially not exceed 200 μm, i.e. the particle size is preferably in the range from 10 μm to 1000 μm, in particular from 15 μm to 500 μm, especially from 20 to 200 μm.

According to the invention, the formation of form Y under the comminuting conditions requires that at least a portion, generally at least 50 wt %, in particular at least 70 wt %, especially at least 80 wt %, or at least 90 wt % or the total amount of the pyripyropene derivative I contained in the slurry being subjected to comminution is present in its form B. Therefore, the aqueous slurry of the coarse particles of the compound of formula I is kept for a time sufficient to achieve partial conversion, generally at least 50% conversion, in particular at least 70% conversion especially at least 80% conversion or complete or almost complete (at least 90%) conversion into form B, i.e. prior to comminution, the portion of the pyripyropene derivative I, which is present in its form B, is generally at least 50 wt %, in particular at least 70 wt %, especially at least 80 wt %, or at least 90 wt % or the total amount of the pyripyropene derivative I contained in the slurry prior to step b).

The time sufficient to achieve partial conversion, generally at least 50% conversion, in particular at least 70% conversion, especially at least 80% conversion or complete or almost complete (at least 90%) conversion into form B will depend on the temperature and the desired degree of conversion. The time required to achieve the desired degree of conversion will generally be at least 0.5 h, in particular at least 1 h or at least 2 h. Generally, complete conversion does not require more than 8 days, in particular not more than 4 days. Higher temperatures accelerate the conversion into form B.

Generally step a2) will be performed at temperatures ranging from 20 to 100° C., in particular from 25 to 95° C. or from 30 to 90° C. Higher temperature may be possible using a pressurized equipment. Lower temperatures may also be possible. In particular, the slurry is kept for a period of at least 0.5 h, e.g. from 1 h to 8 d at a temperature in the range from 25 to 95° C. Especially, the slurry is kept at a temperature from 30 to 90° C. for a period of 2 h to 8 d.

To facilitate the conversion, moderate shear may be applied, e.g. by stirring or rocking. However, during step a2) the particle size of the coarse particles should not be reduced to an average diameter of below 10 μm, in particular below 20 μm, in order to avoid gelling.

The concentration of the pyripyropene derivative I in the slurry is of minor importance. For practical reasons the concentration of the compound of formula I in the aqueous slurry is from 5 to 60 wt %, in particular from 10 to 50 wt %, especially from 15 to 40 wt % by weight, based on the total weight of the aqueous slurry.

The purity of the pyripyropene derivative I used in the method of the present invention is of minor importance. The pyripyropene derivative I will normally have a purity sufficient for its intended use as a pesticide. The purity of the pyripyropene derivative I will be generally at least 90%, in particular at least 95%. The method of the invention has particular benefits, when the pyripyropene derivative I has a purity of at least 97%. Purity has to be understood as the relative amount of pyripyropene derivative I in the organic solid active ingredient suspended in the slurry.

As outlined above, the surfactant may be added at any stage. Preferably, the major amount of surfactant, in particular at least 50 wt %, especially at least 80 wt %, based on the total amount of surfactant added prior to step b), or all of the surfactant is added after completion of step a2, i.e. after the desired degree of conversion into form B has been reached. However, it may also be beneficial to add some of the surfactant, e.g. from 1 to 50 wt %, in particular from 2 to 20 wt %, based on the total amount of surfactant added prior to step b), before the completion of step a2), i.e. during steps a1) or a2). Preferably, the concentration of the surfactant in the slurry during step a2) does not exceed 2 wt %, based on the weight of the slurry. Preferably, the slurry does not contain organic solvents, i.e. the concentration of organic solvent does not exceed 2% by weight, based on the slurry.

According to the invention, the aqueous slurry of the coarse particles of the pyripyropene derivative I, wherein the pyripyropene derivative I is at least partially present as its form B, will be subjected to a comminution step b), where the coarse particles are disintegrated down to the desired particle size in the presence of a surfactant.

The desired particles size, characterized by the volume average diameter of the particles as determined by light scattering, will be generally not exceed 10 μm and in particular not exceed 8 μm or 5 μm. In particular, comminution in step b) is performed to achieve a volume average diameter of the particles of not more than 8 μm, in particular in the range from 0.5 to 5 μm, especially in the range from 0.7 to 3 μm. Preferably the suspended particles after comminution will have a $d_{90}$-value which does not exceed 20 μm, in particular 10 μm, i.e. not more than 10 vol.-% of the particles have a diameter which is above and at least 90 vol.-% of the particles have a diameter which is below the $d_{90}$-value cited. Preferably, the suspended particles after comminution will have a $d_{10}$-value which is not lower than 0.2 μm, in particular not lower than 0.3 μm, i.e. not more than 10 vol.-% of the particles have a diameter which is below the $d_{10}$-value cited and at least 90 vol.-% of the particles have a diameter which is above the $d_{10}$-value cited.

In order to perform step b), the slurry of the compound of formula I containing the surfactant or surfactant mixture is treated in a suitable device which is capable of achieving reduction of the particle size of the coarse particles. Thus, step b) may be carried out by any physical attrition method, such as grinding, crushing or milling, in particular by wet grinding or wet milling, including e.g. bead milling, hammer milling, jet milling, air classifying milling, pin milling, cryogenic grinding processes and the like. In a preferred embodiment of the invention, step b) is carried out by bead milling. In particular, bead sizes in the range of from 0.05 to 5 mm, more particularly from 0.2 to 2.5 mm, and most particularly from 0.5 to 1.5 mm have been found to be suitable. In general, bead loadings in the range of from 40 to 99%, particularly from 70 to 97%, and more particularly from 65 to 95% may be used.

Step b) is carried out in apparatus suitable for this purpose, in particular apparatus suitable for wet grinding or wet milling methods. Such apparatus are generally known. Thus, step (ii) is preferably carried out in mills, such as ball mills or bead mills, agitator ball mills, circulating mills (agitator ball mills with pin grinding system), disk mills, annular chamber mills, double cone mills, triple roll mills, batch mills, colloid mills, and media mills, such as sand mills. To dissipate the heat energy introduced during the grinding process, the grinding chambers are preferably fitted with cooling systems. Particularly suitable is the ball mill Drais Superflow DCP SF 12 from DRAISWERKE, INC. 40 Whitney Road. Mahwah, N.J. 07430 USA, a Drais Perl Mill PMC from DRAISWERKE, INC., the circulating mill system ZETA from Netzsch-Feinmahltechnik GmbH, the disk mill from Netzsch Feinmahltechnik GmbH, Selb, Germany, the bead mill Eiger Mini 50 from Eiger Machinery, Inc., 888 East Belvidere Rd., Grayslake, Ill. 60030 USA and the bead mill DYNO-Mill KDL from WA Bachofen AG, Switzerland.

The time required for reducing the particle size depends in a manner known per se on the desired grade of fineness or the desired particle size of the active compound particle and can be determined by the person skilled in the art in standard experiments. Comminution times in the range of e.g. from 1 to 48 hours have been found to be suitable, although a longer period of time is also conceivable. A comminution time of 2 to 24 hours is preferred.

Typically, the slurry obtained from step a) has a content of the compound of the formula I in the range from 5 to 60 wt %, in particular from 10 to 50 wt %, especially from 15 to 40 wt % by weight, based on the total weight of the aqueous slurry. It has been found beneficial, if the concentration of the compound of formula I in the aqueous suspension during step b) is from 5 to 50 wt %, in particular from 10 to 40 wt %, based on the total weight of the suspension. Thus, the slurry may be used as such or it may be diluted by addition of surfactant and/or water.

According to the invention, step b) is performed in the presence of a surfactant or surfactant mixture, i.e. the aqueous slurry which is subjected to the comminution contains at least one surfactant, which assists stabilization of the fine particles. The amount of surfactant in the aqueous suspension during step b) will generally be at least 1 wt %, in particular at least 2 wt % and is preferably in the range from 1 to 30 wt %, in particular from 2 to 20 wt %, based on the total weight of the aqueous suspension.

Suitable surfactants for step b) are those, which are commonly used as a surfactant for the stabilization of an aqueous suspension concentrate formulation of a solid active ingredient. Suitable surfactants may by anionic or non-ionic.

It has been found advantageous, if the surfactant comprises at least one anionic surfactant. The concentration of anionic surfactant in the suspension during step b) will generally be in the range from 0.1 to 20 wt %, in particular from 0.5 to 15 wt %.

Suitable anionic surfactants are those, which have at least one acidic functional group, which is present in water at pH 7 in its anionic salt form. Suitable functional groups are $SO_3H$, which is present in water at pH 7 as $SO_3^-$, and $PO_3H_2$, which is present in water at pH 7 as $PO_3H^-$ or $PO_3^{2-}$.

Suitable anionic surfactants include anionic emulsifiers and anionic polymeric surfactants. In contrast to anionic emulsifiers, the anionic polymeric surfactants will generally have a molecular weight of above 800 Dalton (number average). Suitable anionic surfactants are alkali metal, alkaline earth metal and ammonium salts of aromatic sulfonic acids, such as benzene sulfonic acid, phenol sulfonic acid, $C_1$-$C_{20}$-alkylbenzene sulfonic acid, naphthalene or alkyl-naphthalene sulfonic such as dibutylnaphthalene-sulfonic acid (Nekal® types, BASF, Germany), alkylsulfonates, alkylarylsulfonates, alkylsulfates, such as laurylether sulfates, fatty alcohol sulfates, such as sulfated lauryl alcohol, sulfated hexa-, hepta- and octadecanolates, sulfated polyethoxylates of fatty alcohols, sulfated polyethoxylates of $C_1$-$C_{20}$-alkylphenols and sulfated polyethoxylates of di- or tristyrylphenol and the anionic polymeric surfactant having a plurality of $SO_3^-$ groups as described hereinafter.

The term "polyethoxylates" means that the compound has a polyethylenoxide radical. In these polyethoxylates the amount of oxyethylene repeating units $CH_2CH_2O$ will usually be in the range from 2 to 100, especially from 4 to 80.

Preferably, the anionic surfactant is selected from anionic polymeric surfactant having a plurality of $SO_3^-$ groups, i.e. at least 2 in particular at least 3 $SO_3^-$ groups. Suitable anionic polymeric surfactants having a plurality of $SO_3^-$ groups include but are not limited to the salts, in particular the alkali metal, alkaline earth metal and ammonium salts, especially the sodium, calcium or ammonium salts of i. condensates of arylsulfonic acids, such as benzene sulfonic acid, phenol sulfonic acid, alkylbenzene sulfonic acid (e.g. toluene sulfonic acid), naphthalene or alkylnaphthalene sulfonic acid such as $C_1$-$C_{10}$-alkylnaphthalene sulfonic acid with formaldehyde and optionally with urea and the salts thereof, e.g. the earth alkaline salts, alkaline salts or ammonium salts, especially the sodium, calcium or ammonium salts;

ii. lignosulfonates and the salts thereof, e.g. the earth alkaline salts, alkaline salts or ammonium salts, especially the sodium, calcium or ammonium salts; and iii. homo- and co-polymers of ethylenically unsaturated sulfonic acids, such as 2-acrylamido-2-methylpropane sulfonic acid, 2-acryloxyethane sulfonic acid, 2-acryloxy-2-methylpropane sulfonic acid, styrenesulfonic acid or vinylsulfonic acid, optionally in the form of a copolymer with a monoethylenically unsaturated monomer, which is e.g. selected from $C_3$-$C_5$ monoethylenically unsaturated carboxylic acid monomers such as acrylic acid or methacrylic acid, $C_1$-$C_6$-alkylesters of $C_3$-$C_5$ monoethylenically unsaturated carboxylic acid monomers such as $C_1$-$C_6$ alkylacrylates and -methacrylates, $C_2$-$C_6$-hydroxyalkylesters of $C_3$-$C_5$ monoethylenically unsaturated carboxylic acid monomers such as $C_2$-$C_6$ hydroxyalkylacrylates and -methacrylates, vinylaromatic monomers such as styrene and $C_2$-$C_{12}$-monolefines such as ethene, propene, 1-butene, isobutene, hexene, 2-ethylhexene, diisobutene (mixture of isobuten dimers), tripropene, tetrapropene, triisobutene etc. and the salts of these homo- and co-polymers, e.g. the earth alkaline salts, alkaline salts or ammonium salts, especially the sodium, calcium or ammonium salts Preferably, the anionic polymeric surfactant having a plurality of $SO_3^-$ groups is selected from the salts of naphthalene sulfonic acid formaldehyde condensates, salts of alkylnaphthalene sulfonic acid formaldehyde condensates and the salts of naphthalene sulfonic acid formaldehyde urea co-condensates. In a particular preferred embodiment, the anionic polymeric surfactant having a plurality of $SO^{3-}$ groups is an alkaline metal salts or earth alkaline metal salt of a reaction product (condensate) of naphthalene sulfonic acid and formaldehyde; particularly suitable examples are the Morwet® grades such as Morwet® D400, D425, D440, D450 or D500 (Akzo Nobel), the Tamol® NN grades of BASF SE, Surfaron® A 1530 N100 or Surfaron® A 1543 N100 (Synthron) and the Tersperse® grades such as Tersperse® 2001, 2020, 2100 or 2425 of Huntsman.

In a particular embodiment, the surfactant comprises at least one non-ionic surfactant in addition to the at least one anionic surfactant. If present, the concentration of non-ionic surfactant in the suspension during step b) will generally be in the range from 0.1 to 20 wt %, in particular from 0.5 to 15 wt %. If present, the weight ratio of non-ionic surfactant to anionic surfactant may be in the range from 10:1 to 1:20, in particular from 5:1 to 1:10.

Suitable non-ionic surfactants are in particular non-ionic emulsifiers having at least one poly($C_2$-$C_4$-alkylenoxide), e.g. polyethoxylates of alkylphenols such as polyoxyethylene octylphenyl ether, polyoxyethylene isooctylphenyl ether, polyoxyethylene nonylphenyl ether, polyoxyethylene tributylphenyl ether, polyoxyethylene tristyrylphenyl ether and polyoxyethylene distyrylphenyl ether, polyethoxylates of fatty alcohols such as polyethoxylates of lauryl alcohol, myristyl alcohol, palmityl alcohol or stearyl alcohol, polyethoxylated castor oil, sorbitol esters, and polymeric non-ionic surfactants having at least one poly($C_2$-$C_4$-alkylenoxide) moiety, which are hereinafter also termed as poly($C_2$-$C_4$-alkylenoxide) polymers. In contrast to non-ionic polymeric surfactants, the non-ionic emulsifiers will generally have a molecular weight of above 1500 Dalton (number average).

A poly($C_2$-$C_4$-alkylenoxide) moiety is an aliphatic polyether moiety, which is constructed of oxy-$C_2$-$C_4$-alkylene repeating units, such as oxyethylene repeating units ($CH_2CH_2O$), oxy-1,2-propylene repeating units [($CH(CH_3)$ $CH_2O$) or ($CH_2CH(CH_3)$ O), respectively], oxy-1,2-butylene, oxy-2,3-butylene, oxy-1,4-butylene or oxy-1,1-dimethyl-1,2-ethylene repeating units [($C(CH_3)_2CH_2O$) or ($CH_2CH(CH_3)_2O$), respectively].

Preferably, the non-ionic surfactant is selected from poly($C_2$-$C_4$-alkylenoxide) polymers. Examples of poly($C_2$-$C_4$-alkylenoxide) polymers are non-ionic copolymers of ethyleneoxide and $C_3$-$C_4$-alkylene oxide which oxyethylene repeating units and oxy-$C_3$-$C_4$-alkylene repeating units, in particular block-copolymers having at least one poly(ethylenoxide) moiety PEO and at least one aliphatic polyether moiety PAO derived from $C_3$-$C_4$-alkylene oxides, in particular polyoxyethylene-polyoxypropylene-blockcopolymers. Further examples of poly($C_2$-$C_4$-alkyleneoxide) polymers are non-ionic graft copolymers containing polyethylene oxide moiety PEO grafted on a non-ionic, hydrophilic polymeric backbone.

Amongst the poly($C_2$-$C_4$-alkyleneoxide) polymers particular preference is given to poly(ethyleneoxide-co-propyleneoxide) polymers, in particular to those poly(ethyleneoxide-co-propyleneoxide) polymers, wherein the ethyleneoxide and propyleneoxide repeating units are arranged blockwise. Amongst the poly($C_2$-$C_4$-alkyleneoxide) polymers particular preference is given to poly(ethyleneoxide-co-propyleneoxide) polymers having a HLB value (HLB=hydrophilic-lipophilic balance) of at least 12, preferably at least 14, in particular at least 15, e.g. from 12 to 20, preferably from 14 to 19, in particular from 15 to 19, in particular to those poly(ethyleneoxide-co-propyleneoxide) polymers, wherein the ethyleneoxide and propyleneoxide repeating units are arranged blockwise. The HLB value referred to herein is the HLB value according to Griffin (W. C. Griffin, J. Soc. Cosmet. Chem. 1, 311 (1950); 5, 249 (1954)—see also H. Mollet et al. "Formulation Technology", 1$^{st}$ ed. Wiley-VCH Verlags GmbH, Weinheim 2001, pages 70-73 and references cited therein). Preferred poly($C_2$-$C_4$-alkyleneoxide) polymers have a number average molecular weight in the range from 1500 to 50000 Dalton, in particular in the range from 1700 to 25000 Dalton.

Particular preference is given to non-ionic surfactant which are selected from the group of non-ionic block-copolymers. These non-ionic block copolymers preferably comprise at least one poly(ethylene oxide) moiety PEO and at least one hydrophobic polyether moiety PAO. The PAO moiety usually comprises at least 3, preferably at least 5, in particular 10 to 100 repeating units (number average) which are derived from $C_3$-$C_4$ alkylene oxides, such as propylene oxide, 1,2-butylene oxide, cis- or trans-2,3-butylene oxide or isobutylene oxide. Preferably, the PAO moieties comprise at least 50% by weight, and more preferably at least 80% by weight of repeating units derived from propylene oxide. The PEO moieties usually comprise at least 3, preferably at least 5, and more preferably at least 10 repeating units derived from ethylene oxide (number average). The weight ratio of PEO moieties and PAO moieties (PEO:PAO) usually ranges from 1:10 to 10:1, preferably from 1:2 to 5:1, more preferably from 1:1 to 4:1 and in particular from 1.1:1 to 3:1. Those are preferred which have a number average molecular weight $M_N$ ranging from more than 1500 to 100000 Dalton, preferably from 1700 to 25000 Dalton, more preferably from 2000 to 20000 Dalton. In general, the PEO moieties and the PAO moieties make up at least 80% by weight, and preferably at least 90% by weight, e.g. 90 to 99.5% by weight, of the non-ionic block copolymer surfactants.

Suitable blockcopolymers are described e.g. in WO2006/002984, in particular those having the formulae P1 to P5 given therein. The non-ionic block copolymer surfactants herein are commercially available e.g. under the trade names Pluronic®, such as Pluronic® P 65, P84, P 103, P 105, P 123 and Pluronic® L 31, L 43, L 62, L 62 LF, L 64, L 81, L 92 and L 121, Pluraflo® such as Pluraflo® L 860, L1030 and L 1060; Pluriol® such as Pluriol® WSB-125, Tetronic®, such as Tetronic® 704, 709, 1104, 1304, 702, 1102, 1302, 701, 901, 1101, 1301 (BASF SE), Agrilan® AEC 167 and Agrilan® AEC 178 (Akcros Chemicals), Antarox® B/848 (Rhodia), Berol® 370 and Berol® 374 (Akzo Nobel Surface Chemistry), Dowfax® 50 C15, 63 N10, 63 N30, 64 N40 and 81 N10 (Dow Europe), Genapol® PF (Clariant), Monolan®, such as Monolan® PB, Monolan® PC, Monolan® PK (Akcros Chemicals), Panox® PE (Pan Asian Chemical Corporation), Symperonic®, such as Symperonic® PE/L, Symperonic® PE/F, Symperonic® PE/P, Symperonic® PE/T (ICI Surfactants), Tergitol® XD, Tergitol® XH and Tergitol® XJ (Union Carbide), Triton® CF-32 (Union Carbide), Teric PE Series (Huntsman) and Witconol®, such as Witconol® APEB, Witconol® NS 500 K and the like.

Likewise particular preference is given to poly(ethoxylate-co-propoxylates) of $C_1$-$C_{10}$ alkanols, having a number average molecular weight $M_N$ of from 1500 to 20000 Dalton Particularly preferred examples include Atlox® G 5000 (Akzo Nobel), Tergitol®XD, Pluronic® P105 and Pluriol® WSB-125 and the like.

Preferred non-ionic graft copolymers contain, in polymerised form, (i) methyl esters or hydroxyl-$C_2$-$C_3$-alkyl esters of $C_3$-$C_5$ monoethylenically unsaturated carboxylic acid monomers, such as methyl acrylate, methyl methacrylate, hydroxyethyl acrylate and hydroxyethyl methacrylate and (ii) polyethylenoxide groups which are attached either via ester linkages or ether linkages to the polymer backbone. In a preferred embodiment, the backbone of these graft copolymers contains, in polymerized form, methyl methacrylate and polyethylene oxide esters of methacrylic acid, a particularly suitable example being Atlox® 4913 (Akzo Nobel), and the like.

Although, the temperature during step b) is of minor importance, it has been found advantageous to perform step b) in a manner that the temperature of the suspension does not exceed 50° C. Generally, step b) is performed at a temperature above 0° C. In particular a temperature in the range of from 2° C. to 40° C. have been found to be suitable. As the comminution introduces energy into the suspension, temperature can be simply maintained in these ranges by cooling.

The pressure conditions during comminution are generally not critical; thus, for example, atmospheric pressure has been found to be suitable.

To the aqueous formulation obtained from step b), one or more further formulation additives, e.g. rheology modifiers (i.e. thickeners), preservatives, antifoam and/or antifreeze, may be added, optionally together with further water and/or surfactant, if required.

As explained above, the pyripyropene derivative I is at least partially converted into its form Y during its comminution. In particular, the pyripyropene derivative I is converted into its form Y to an extent of generally at least 50 wt %, in particular at least 70 wt %, especially at least 80 wt %, completely or almost completely (i.e. at least 90 wt %), based on the total amount of the pyripyropene derivative I present during step b). Thus, in the obtained suspension, and thus also in the suspension concentrate formulation of the present invention, the pyripyropene derivative I is at least partially present in its form Y, frequently to an extent of at least 50 wt %, in particular at least 70 wt %, especially at least 80 wt %, completely or almost completely (i.e. at least 90 wt %), based on the total amount of the pyripyropene derivative in the suspension concentrate formulation.

The aqueous formulation shows increased storage stability, in particular no or no significant increase in particle size of the suspended particles, e.g. due to unwanted Ostwald's ripening or agglomeration, is observed upon storage.

The novel aqueous suspension concentrate formulation of the present invention preferably contains a) 1 to 30 wt %, in particular 2 to 25 wt %, especially 3 to 15 wt %, based on the total weight of the formulation, of the pesticide compound of formula I, which is at least partially or preferably to an extent of at least 90% or completely present in its form Y;

b) 0.1 to 20 wt %, in particular 1 to 15 wt %, especially 1.5 to 12 wt %, based on the total weight of the formulation, of at least one anionic surfactant as defined above, where the anionic surfactant preferably comprises at least one anionic polymeric surfactant having a plurality of $SO^{3-}$ groups or which is preferably selected from anionic polymeric surfactants having a plurality of $SO^{3-}$ groups;

c) 0.1 to 20 wt %, in particular from 1 to 15 wt %, especially 1.5 to 10 wt %, based on the total weight of the formulation, of at least one non-ionic surfactant, which preferably comprises at least one poly($C_2$-$C_4$-alkylenoxide) polymer or is in particular selected from poly($C_2$-$C_4$-alkylenoxide) polymers, d) 40 to 98.8 wt %, in particular 50 to 98 wt %, especially 60 to 97 wt %, based on the total weight of the formulation, by weight of water.

The anionic surfactant of component b) preferably comprises at least one anionic polymeric surfactant having a plurality of $SO^{3-}$ groups as defined above, which is in particular selected from the salts of naphthalene sulfonic acid formaldehyde condensates, salts of alkylnaphthalene sulfonic acid formaldehyde condensates and the salts of naphthalene sulfonic acid formaldehyde urea co-condensates. Preferred salts of these surfactants are the alkalimetal salts, the earthalkaline metal salts and the ammonium salts, in particular the sodium salts, the calcium salts and the ammonium salts. In particular, the polymeric surfactant having a plurality of $SO^{3-}$ groups amounts to at least 90 wt % of the anionic surfactant contained in the formulation of the present invention.

The non-ionic surfactant of component c) preferably comprises at least one non-ionic polymeric surfactant, which is in particular selected from the group of poly($C_2$-$C_4$-alkyleneoxide) polymers as defined above. With regard to the preferred poly($C_2$-$C_4$-alkyleneoxide) polymers the above statements also apply to component c). Amongst the poly($C_2$-$C_4$-alkyleneoxide) polymers particular preference is given to poly(ethyleneoxide-co-propyleneoxide) polymers, in particular to those poly(ethyleneoxide-co-propyleneoxide) polymers, wherein the ethyleneoxide and propyleneoxide repeating units are arranged blockwise. Amongst the poly($C_2$-$C_4$-alkyleneoxide) polymers particular preference is given to poly(ethyleneoxide-co-propyleneoxide) polymers having a HLB value (HLB=hydrophilic-lipophilic balance) of at least 12, preferably at least 14, in particular at least 15, e.g. from 12 to 20, preferably from 14 to 19, in particular from 15 to 19, in particular to those poly(ethyleneoxide-co-propyleneoxide) polymers, wherein the ethyleneoxide and propyleneoxide repeating units are arranged blockwise. In particular, the poly($C_2$-$C_4$-alkyleneoxide) polymers as defined above amount to at least 90 wt % of the non-ionic surfactant contained in the formulation of the present invention. In particular, the non-ionic surfactant is selected from the group consisting of the aforementioned poly($C_2$-$C_4$-alkyleneoxide) polymers.

The desired particles size, characterized by the volume average diameter of the particles as determined by light scattering, will be generally not exceed 10 µm and in particular not exceed 8 µm or 5 µm. In particular, comminution in step b) is performed to achieve a volume average diameter of the particles of not more than 8 µm, in particular in the range from 0.5 to 5 µm, especially in the range from 0.7 to 3 µm. Preferably the suspended particles after comminution will have a $d_{90}$-value which does not exceed 20 µm, in particular 10 µm, i.e. not more than 10 vol.-% of the particles have a diameter which is above and at least 90 vol.-% of the particles have a diameter which is below the $d_{90}$-value cited. Preferably the suspended particles after comminution will have a $d_{10}$-value which is not lower than 0.2 µm, in particular not lower than 0.3 µm, i.e. not more than 10 vol.-% of the particles have a diameter which is below the $d_{10}$-value cited and at least 90 vol.-% of the particles have a diameter which is above the $d_{10}$-value cited.

The aqueous formulations according to the invention may also comprise customary additives, for example viscosity-modifying additives (thickeners), antifoams, bactericides and antifreeze agents. The amount of additives will generally not exceed 5% by weight, in particular 2% by weight of the total weight of the composition.

Suitable thickeners are compounds which confer a pseudoplastic flow behavior to the formulation, i.e. high viscosity at rest and low viscosity in the agitated stage. Mention may be made, in this connection, for example, of commercial thickeners based on polysaccharides, such as Xanthan Gum® (Kelzan® from Kelco; Rhodopol® 23 from Rhone Poulenc or Veegum® from R.T. Vanderbilt), or phyllosilicates which may be hydrophobized, such as Attaclay® (from Engelhardt). Xanthan Gum® is a preferred thickener.

Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof.

Bactericides can be added to stabilize the compositions according to the invention against attack by microorganisms. Suitable bactericides are, for example, based on isothiazolones such as the compounds marketed under the trademarks Proxel® from Avecia (or Arch) or Acticide® RS from Thor Chemie and Kathon® MK from Rohm & Haas.

The invention also relates to aqueous ready-to-use preparations obtained by diluting the formulation of the invention with water, generally with at least 5 parts of water, preferably at least 10 parts of water, in particular at least 20 parts of water and more preferably at least 50 parts of water, e.g. from 10 to 10,000, in particular from 20 to 1,000 and more preferably from 50 to 250 parts of water per one part of the liquid formulation (all parts are given in parts by weight).

Dilution will be usually achieved by pouring the liquid concentrate formulation of the invention into water. Usually, dilution is achieved with agitation, e.g. with stirring, to ensure a rapid mixing of the concentrate in water. However, agitation is generally not necessary. Though the temperature of mixing is not critical, mixing is usually performed at temperatures ranging from 0 to 100° C., in particular from 10 to 50° C. or at ambient temperature.

The water used for mixing is usually tap water. However the water may already contain water soluble compounds which are used in plant protection, e.g. nutrificants, fertilizers or water soluble pesticides.

The formulations of the invention can be applied in a conventional manner, e.g. in diluted form as an aqueous ready-to-use preparation described above. The inventive aqueous ready-to-use preparations can be applied by spraying, in particular spraying of the leaves. Application can be carried out using spraying techniques known to the person skilled in the art, for example using water as carrier and amounts of spray liquor of about 100 to 1000 liters per hectare, for example from 300 to 400 liters per hectare.

The present invention further relates to a method for controlling insects, arachnids or nematodes comprising contacting an insect, acarid or nematode or their food supply, habitat, breeding grounds or their locus with an inventive formulation or preparation in pesticidally effective amounts.

The inventive composition exhibits outstanding action against animal pests (e.g. insects, acarids or nematodes) from the following orders:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Pieris rapae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*;

beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Cric-* eris asparagi, Ctenicera ssp., Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga sp., Phyllopertha horticola, Phyllotreta nemorum, Phyllotreta striolata, Popillia japonica, Sitona lineatus and Sitophilus granaria;

flies, mosquitoes (Diptera), e.g. Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates spp., Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga spp., Simulium vittatum, Stomoxys calcitrans, Tabanus bovinus, Tabanus atratus, Tabanus lineola, and Tabanus similis, Tipula oleracea, and Tipula paludosa; thrips (Thysanoptera), e.g. Dichromothrips corbetti, Dichromothrips ssp., Frankliniella fusca, Frankliniella occidentalis, Frankliniella tritici, Scirtothrips citri, Thrips oryzae, Thrips palmi and Thrips tabaci, termites (Isoptera), e.g. Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis, and Coptotermes formosanus;

cockroaches (Blattaria—Blattodea), e.g. Blattella germanica, Blattella asahinae, Periplaneta americana, Periplaneta japonica, Periplaneta brunnea, Periplaneta fuliginosa, Periplaneta australasiae, and Blatta orientalis;

bugs, aphids, leafhoppers, whiteflies, scale insects, cicadas (Hemiptera), e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma spp., and Arilus critatus;

ants, bees, wasps, sawflies (Hymenoptera), e.g. Athalia rosae, Atta cephalotes, Atta capiguara, Atta cephalotes, Atta laevigata, Atta robusta, Atta sexdens, Atta texana, Crematogaster spp., Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus spp., Vespula squamosa, Paravespula vulgaris, Paravespula pennsylvanica, Paravespula germanica, Dolichovespula maculata, Vespa crabro, Polistes rubiginosa, Camponotus floridanus, and Linepithema humile;

crickets, grasshoppers, locusts (Orthoptera), e.g. Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera, and Locustana pardalina;

arachnoidea, such as arachnids (Acarina), e.g. of the families Argasidae, Ixodidae and Sarcoptidae, such as Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei, and Eriophyidae spp. such as Aculus schlechtendali, Phyllocoptrata oleivora and Eriophyes sheldoni; Tarsonemidae spp. such as Phytonemus pallidus and Polyphagotarsonemus latus; Tenuipalpidae spp. such as Brevipalpus phoenicis; Tetranychidae spp. such as Tetranychus cinnabarinus, Tetranychus kanzawai, Tetranychus pacificus, Tetranychus telarius and Tetranychus urticae, Panonychus ulmi, Panonychus citri, and Oligonychus pratensis; Araneida, e.g. Latrodectus mactans, and Loxosceles reclusa;

fleas (Siphonaptera), e.g. Ctenocephalides felis, Ctenocephalides canis, Xenopsylla cheopis, Pulex irritans, Tunga penetrans, and Nosopsyllus fasciatus, silverfish, firebrat (Thysanura), e.g. *Lepisma saccharina* and *Thermobia domestica*,
centipedes (Chilopoda), e.g. *Scutigera coleoptrata*,
millipedes (Diplopoda), e.g. *Narceus* spp.,
earwigs (Dermaptera), e.g. *forficula auricularia*,
lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*.
Collembola (springtails), e.g. *Onychiurus* ssp.

The formulations and preparations of the present invention are also suitable for controlling nematodes: plant parasitic nematodes such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Helicotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The formulations and preparations according to the invention can be applied to any and all developmental stages of pests, such as egg, larva, pupa, and adult. The pests may be controlled by contacting the target pest, its food supply, habitat, breeding ground or its locus with a pesticidally effective amount of the inventive formulations and preparations. "Locus" means a plant, plant propagation material (preferably seed), soil, area, material or environment in which a pest is growing or may grow.

In general, "pesticidally effective amount" means the amount of the inventive formulations and preparations needed to achieve an observable effect on growth, including the effects of necrosis, death, retardation, prevention, and removal, destruction, or otherwise diminishing the occurrence and activity of the animal pest. The pesticidally effective amount can vary for the various formulations and preparations used in the invention. A pesticidally effective amount of the formulations and preparations will also vary according to the prevailing conditions such as desired pesticidal effect and duration, weather, target species, locus, mode of application, and the like.

The inventive formulations and preparations are employed by treating the animal pest or the plants, plant propagation materials (preferably seeds), materials or soil to be protected from pesticidal attack with a pesticidally effective amount of the active compounds. The application can be carried out both before and after the infection of the materials, plants or plant propagation materials (preferably seeds) by the pests.

Preferably, the inventive formulations and preparations are employed by treating the animal pests or the plants or soil to be protected from pesticidal attack via foliar application with a pesticidally effective amount of the active compounds. In addition, the application can be carried out both before and after the infection of the plants by the pests.

In the method of combating animal pests (insects, acarids or nematodes) the application rates of the formulations and preparations according to the invention depend on the intensity of the infestation by pests, on the development phase of the plants, on the climatic conditions at the application site, on the application method, on whether pyripyropene derivative I is used solely or in combination with further active compounds and on the desired effect. In general, the application rate is in the range of from 0.1 g/ha to 10000 g/ha, preferably 1 g/ha to 5000 g/ha, more preferably from 20 to 1000 g/ha, most preferably from 10 to 750 g/ha, in particular from 20 to 500 g/ha of total active compound.

In the context of the present invention, the term plant refers to an entire plant, a part of the plant or the propagation material of the plant.

Plants and as well as the propagation material of said plants, which can be treated with the inventive formulations and preparations include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

For example, formulations and preparations according to the present invention can be applied (as seed treatment, spray treatment, in furrow or by any other means) also to plants which have been modified by breeding, mutagenesis or genetic engineering including but not limiting to agricultural biotech products on the market or in development (cf. http://www.bio.org/speeches/pubs/er/agri_products.asp).

Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the Mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The inventive formulations and preparations are effective through both contact (via soil, glass, wall, bed net, carpet, plant parts or animal parts), and ingestion (bait, or plant part) and through trophallaxis and transfer.

Preferred application methods are into water bodies, via soil, cracks and crevices, pastures, manure piles, sewers, into water, on floor, wall, or by perimeter spray application and bait.

Methods to control infectious diseases transmitted by non-phytophathogenic insects (e.g. malaria, dengue and yellow fever, lymphatic filariasis, and leishmaniasis) with the inventive formulations and their respective preparations or compositions also comprise treating surfaces of huts and houses, air spraying and impregnation of curtains, tents, clothing items, bed nets, tsetse-fly trap or the like. Insecticidal compositions for application to fibers, fabric, knit-goods, non-wovens, netting material or foils and tarpaulins preferably comprise a composition including an inventive formulation, optionally a repellent and at least one binder.

The inventive formulations and preparations can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities).

In the case of soil treatment or of application to the pests dwelling place or nest, the quantity of active compound ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

The invention further relates to methods for protection of plant propagation material, termed herein also methods for seed treatment, which methods comprise contacting the plant propagation material with a formulation or preparation of the invention or a composition derived therefrom in pesticidally effective amounts. The methods for seed treatment comprise all suitable methods known to the person skilled in the art for treating seed, such as, for example, seed dressing, seed coating, seed soaking, seed film coating, seed multilayer coating, seed encrusting, seed dripping, seed dusting and seed pelleting.

The formulations and preparations of the invention can be used as is for seed treatment. Alternatively, the inventive formulations and preparations can be converted into compositions for seed treatment using methods known to skilled person, e.g. by adding auxiliaries such as colorants, tackifiers or binders.

In a first embodiment of seed treatment according to the invention, the seed, i.e. the plant product capable of propagation, intended for sowing, is treated with an inventive formulation or preparation, or an composition derived therefrom. Here, the term seed comprises seeds and plant parts capable of propagation of any type, including seeds, seed grains, parts of seeds, seedlings, seedlings' roots, saplings, shoots, fruits, tubers, cereal grains, cuttings and the like, in particular grains and seeds.

Alternatively, the seed may also be treated with the inventive formulation or preparation, or a composition derived therefrom, during sowing. In a further embodiment of seed treatment or soil treatment according to the invention, the furrows are treated with the inventive formulation or preparation, or an composition derived therefrom, either before or after sowing of the seed.

In a preferred embodiment of the invention, the inventive formulations or preparations are used for the protection of seeds, seedlings' roots or shoots, preferably seeds.

The seeds which have been treated in accordance with the invention are distinguished by advantageous properties in comparison with conventionally treated seeds and therefore also form part of the subject matter of the present application. The seeds treated this way comprise the inventive formulation generally in an amount of from 0.1 g to 10 kg per 100 kg of seed, preferably 0.1 g to 1 kg per 100 kg of seed.

The following examples and figures further illustrate the present invention:

FIG. 1: X-ray Powder Diffractogramm (XRPD) of Form Y, obtained from the suspension concentrate of example 1.

Figure 2:
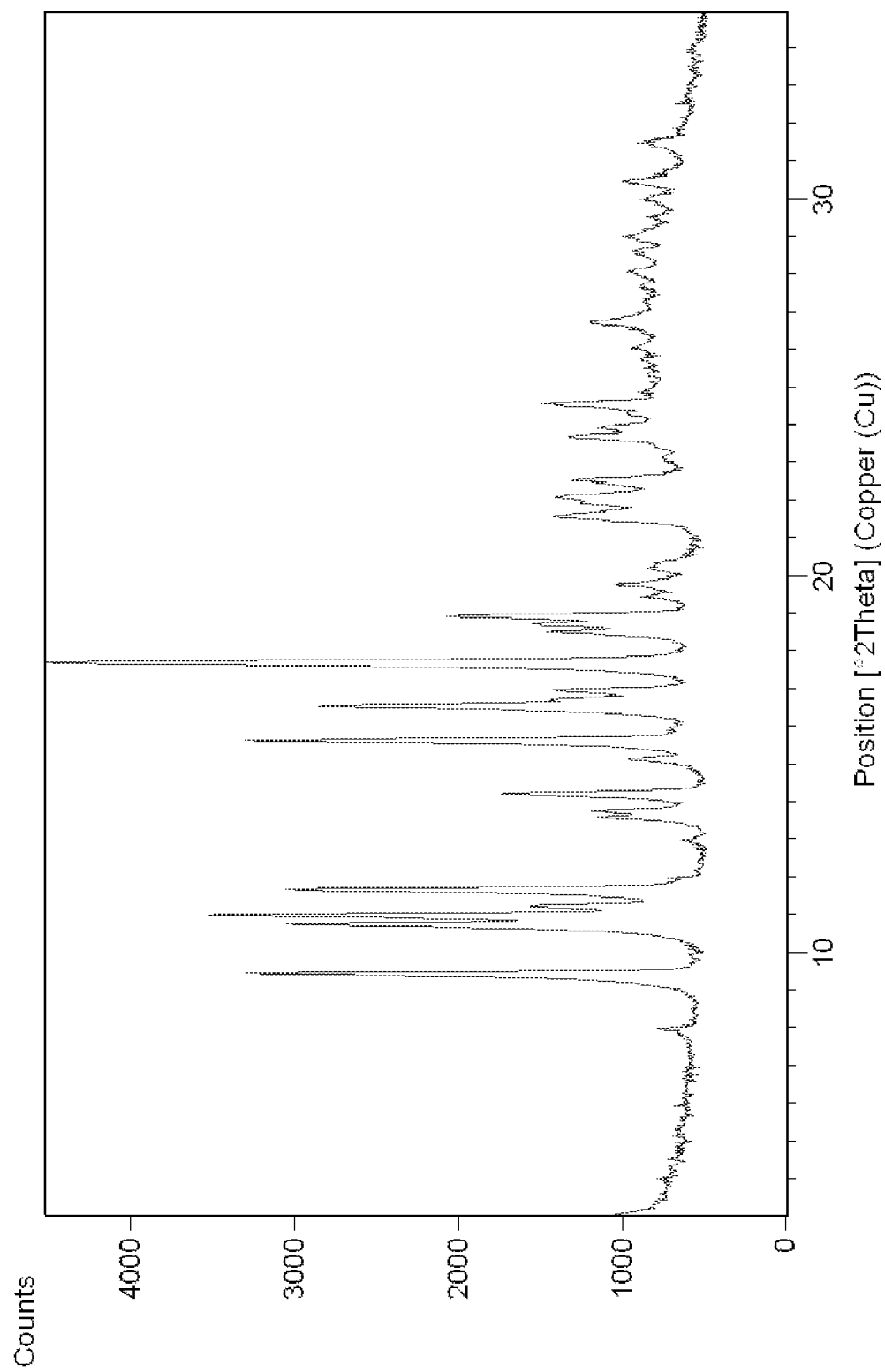

FIG. 2: X-ray powder diffractogramm (XRPD) of Form B, obtained from the slurry of example 1.

STARTING MATERIALS

Insecticide A: Compound of formula I having a purity of >97.5%, amorphous.
Insecticide B: Compound of formula I having a purity of 93-94%.
Surfactant 1: Sodium salt of a naphthalene sulfonic acid formaldehyde condensate—Morwet® D425 (Akzo Nobel).
Surfactant 2: Sodium salt of a naphthalene sulfonic acid formaldehyde condensate—Wettol D1 (BASF SE).
Surfactant 3: $C_1$-$C_3$-alkylether of poly-$C_2$-$C_3$-alkylene glycol ($M_N$ 2900)—Atlox®G5000 (Croda), HLB 17.
Surfactant 4: EO/PO triblock copolymer having a molecular weight of 6500 and a propylene oxide percentage of 50% by weight.
Antifoaming agent: Silicon based defoamer—Silicon SRE-PFL (Wacker).
Preservative: Isothiazolinone—Acticide MBS (Thor).
Thickener: Xanthan Gum.
Analytics:

The X-ray powder diffractograms (XRPD) reported herein and displayed in FIGS. 1 and 2 were recorded using a Panalytical X'Pert Pro diffractometer (manufacturer: Panalytical) in reflection geometry in the range from 2θ=3°-35° C. with increments of 0.0167° C. using Cu-Kα radiation (at 25° C.). The recorded 2θ values were used to calculate the stated interplanar spacings d. The intensity of the peaks (y-axis: linear intensity counts) is plotted versus the 2θ angle (x-axis in degrees 2θ).

Particle Size distributions were determined by using a Malvern Mastersizer 2000 by using a 0.1-1% dilution of the respective specimen in water.

Viscosity of the formulation was determined at 20° C. by using AR 2000ex Rheometer of TA instruments.

Dilution stability was determined by diluting 1 ml of the formulation with 200 ml of deionized water and pouring the mixture into a scaled cone-shaped beaker to determine the amount of sediments.

EXAMPLE 1—STABLE SUSPENSION CONCENTRATE

An aqueous suspension concentrate (SC A) having the following composition was prepared by the process of the invention: 100 g/l of Insecticide A, 106 g/l of surfactant 1 31.8 g/l of surfactant 3, 10 wt %, 2.1 g/l of xanthan gum, 4.2 g/l of antifoaming agent, 0.16 wt % preservative and water up to 1 L.

The formulation was prepared as follows:
(a) 30 parts by weight of Insecticide A, in the form of a powder, and 70 parts by weight of water were mixed in a vessel to obtain an aqueous slurry. The particle diameter of the particles was in the range 30-800 μm. The slurry was warmed to the desired temperature and stirring was continued until a XRPD of a sample taken from the slurry showed a conversion of at least 90% into form B. The time required for conversion is summarized in table 1.

The slurry was allowed to cool to 22° C. and transferred in a suitable vessel and mixed with the required amounts of surfactant 1 (31.8 parts by weight) and surfactant 3 (9.54 parts by weight) and about 50% of the required amount of antifoaming agent (0.63 parts by weight) by using a high shear mixer.

b) The mixture was then ground in a bead mill with sufficient ball loading to ensure effective milling efficiency. The temperature of grinding head was controlled at 5° C. The milling was stopped when an average particle size of 1.5-2 μm (volume average) had been achieved (measured with Malvern Mastersizer 2000). To the thus obtained suspension the remaining antifoaming agent, the preservative and the thickener and water were added to with stirring to ensure homogeneous distribution of components. The amount of water was chosen that the final concentration of the pyripyropene derivative in the formulation was 100 g/l.

The apparent viscosity of the fresh prepared formulation at 20° C. was 29 mPas (shear rate 100 s$^{-1}$) and the true viscosity was 16 mPas.

The volume average particle size of the pesticide particles in the fresh prepared formulation was 2.2 μm ($d_{50}$ value), the $d_{90}$ value was 398 μm (after short sonication the $d_{50}$ value decreased to about 3.8 μm, indicating that some agglomerates have been formed), 48 wt % of the particles had a diameter of <2 μm (after short sonication 79.5 wt %).

Upon dilution of 1 ml of the formulation with 200 ml of deionized water less than 0.05 ml of sediment formed, indicating high dilution stability.

EXAMPLE 2—STABLE SUSPENSION CONCENTRATE

An aqueous suspension concentrate (SC A) having the following composition was prepared by the process of example 1: 100 g/l of Insecticide B, 106 g/l of surfactant 1 31.8 g/l of surfactant 3, 10 wt %, 2.1 g/l of xanthan gum, 4.2 g/l of antifoaming agent, 0.16 wt % preservative and water up to 1 L.

The apparent viscosity of the fresh prepared formulation at 20° C. was 23 mPas (shear rate 100 s$^{-1}$) and the true viscosity was 15 mPas.

The volume average particle size of the pesticide particles in the fresh prepared formulation was 0.7 μm ($d_{50}$ value), the $d_{90}$ value was 2.4 μm, 88 wt % of the particles had a diameter of <2 μm.

Upon dilution of 1 ml of the formulation with 200 ml of deionized water less than 0.05 ml of sediment formed, indicating high dilution stability.

TABLE 1

| Conversion times: | | |
|---|---|---|
| T [° C.] [1)] | | Conversion time |
| Insecticide A | 20° C. | <8 d |
| Insecticide A | 40° C. | <48 h |
| Insecticide A | 60° C. | 12 h |

EXAMPLE 3—STABLE SUSPENSION CONCENTRATE

An aqueous suspension concentrate (SC A) having the following composition was prepared by the process of example 1: 100 g/l of Insecticide A, 30 g/l of surfactant 2, Wl of surfactant 4, 2.1 g/l of xanthan gum, 4.2 g/l of antifoaming agent, 0.16 wt % preservative and water up to 1 L.

The apparent viscosity of the fresh prepared formulation at 20° C. was 40 mPas (shear rate 100 s$^{-1}$) and the true viscosity was 17 mPas.

The volume average particle size of the pesticide particles in the fresh prepared formulation was 3 μm ($d_{50}$ value), the $d_{90}$ value was 7.5 μm, 34 wt % of the particles had a diameter of <2 μm.

Upon dilution of 1 ml of the formulation with 200 ml of deionized water less than 0.05 ml of sediment formed, indicating high dilution stability.

COMPARATIVE EXAMPLE 1—INSTABLE SUSPENSION CONCENTRATE

An aqueous suspension concentrate (SC A) having the following composition was prepared by the process described hereinafter: 100 g/l of Insecticide A, 106 g/l of surfactant 1 31.8 g/l of surfactant 3, 10 wt %, 2.1 g/l of xanthan gum, 4.2 g/l of antifoaming agent, 0.16 wt % preservative and water up to 1 L.

30 parts by weight of insecticide A, 70 parts by weight of water, 31.8 parts by weight of surfactant 1, 9.54 parts by weight of surfactant 3 and about 50% of the required amount of antifoaming agent (0.63 parts by weight) were mixed together in a suitable container using a high shear mixer. The mixture was then ground in a bead mill with sufficient ball loading to ensure effective milling efficiency. The temperature of grinding head was controlled at 5° C. During milling the viscosity increased and milling had to be stopped. To the thus obtained suspension the remaining antifoaming agent, the preservative and the thickener and water were added to with stirring to ensure homogeneous distribution of components. The amount of water was chosen that the final concentration of the pyripyropene derivative in the formulation was 100 g/l.

The apparent viscosity of the fresh prepared formulation at 20° C. was 147 mPas (shear rate 100 s$^{-1}$) and the true viscosity was 91 mPas.

The volume average particle size of the pesticide particles in the fresh prepared formulation was 9.3 μm ($d_{50}$ value), the $d_{90}$ value was 307.1 μm (after short sonication the $d_{50}$ value decreased to about 16.7 μm, indicating that some agglomerates have been formed), 13.6 wt % of the particles had a diameter of <2 μm (after short sonication 23.3 wt %).

Upon dilution of 1 ml of the formulation with 200 ml of deionized water 0.5 ml of sediment formed, indicating poor dilution stability.

COMPARATIVE EXAMPLE 2—INSTABLE SUSPENSION CONCENTRATE

The method of comparative example 1 was repeated but using Insecticide B instead of Insecticide A.

The apparent viscosity of the fresh prepared formulation at 20° C. was 36 mPas (shear rate 100 s$^{-1}$) and the true viscosity was 30 mPas.

The volume average particle size of the pesticide particles in the fresh prepared formulation was 5.0 μm ($d_{50}$ value), the $d_{90}$ value was 10.2 μm, 16.1 wt % of the particles had a diameter of <2 μm.

Upon dilution of 1 ml of the formulation with 200 ml of deionized water less than 0.05 ml of sediment formed, indicating high dilution stability.

Tests of Storage Stability:

Samples of the formulations of examples 1 and 2 were stored for two weeks at different storage conditions and before and thereafter analyzed with regard to the particle size of the suspended particles, viscosity and dilution stability. The results are summarized in table 2.

TABLE 2

| Example 1, Comparative Example 1 | | | | | | |
|---|---|---|---|---|---|---|
| | Example 1 | | | Comparative Example 1 | | |
| | initial | Stor. A [1] | Stor. B [2] | initial | Stor. A [1] | Stor. B [2] |
| $d_{50}$ [μm] [3] | 2.2 | 1.2 | 1.0 | 9.3/4.7 | 2.7/1.7 | 2.0/1.2 |
| $d_{90}$ [μm] [3] | 378/3.8 | 130/2.4 | 43.0/3.5 | 307/16.7 | 10.9/5.7 | 248/4.0 |
| <2 μm [wt %] | 48.8 | 27.9 | 73.6 | 13.6 | 39.2 | 50.0 |
| Vis(t) [mPas] [4] | 16 | 17 | 14 | 91 | 65 | 24 |
| Vis(a) [mPas] [5] | 29 | 28 | 25 | 147 | 111 | 49 |
| Sediment [ml] [6] | <0.05 | <0.05 | <0.05 | 0.5 | 0.5 | 0.5 |
| | Example 2 | | | Comparative Example 2 | | |
| | initial | Stor. A [1] | Stor. B [2] | initial | Stor. A [1] | Stor. B [2] |
| $d_{50}$ [μm] [3] | 0.7 | 1.3 | 3.9/0.7 | 5.0/3.0 | 21.9/3.2 | 23.7/8.3 |
| $d_{90}$ [μm] [3] | 2.4 | 3.6 | 618/2.5 | 10.2/6.5 | 207/14.5 | 166/28.4 |
| <2 μm [wt %] | 88.2 | 71.8 | 41.9 | 16.1 | 11.0 | 8.1 |
| Vis(t) [mPas] [4] | 15 | 22 | 15 | 30 | 36 | 21 |
| Vis(a) [mPas] [5] | 23 | 35 | 23 | 36 | 53 | 73 |
| Sediment [ml] [6] | <0.05 | <0.05 | <0.05 | <0.05 | 0.8 | 1.1 |

[1] Storage condition A: 2 weeks at 54° C.
[2] Storage condition B: 2 weeks at −10° C./+10° C. with a cycling rate of 24 h.
[3] $d_{90}$ value before/after sonication
[4] true viscosity
[5] apparent viscosity
[6] amount of sediment upon dilution Two further samples of examples 1, 2 and 3 were stored at −20° C. as well as 60° C. for one month, respectively. The crystal form before/after storage was characterized by XRPD.

The X-ray powder diffractogram of the formulation of example 1, measured at 25° C. and Cu-K$_\alpha$ radiation, before storage is depicted as FIG. 1 and shows the following reflexes, given as 2θ values: 9.7±0.2°, 10.3±0.2°, 11.3±0.2°, 14.0±0.2°, 15.5±0.2°, 16.4±0.2°, 17.6±0.2°. A similar XRPD was found after storage for 2 weeks at 54° C. with same reflexes, indicating that the form Y was present in the formulation before and after storage.

Same results were found for the formulation of examples 2 and 3.

We claim:

1. A method for producing an aqueous suspension concentrate formulation of a compound of formula I in the form of fine particles;

Formula I

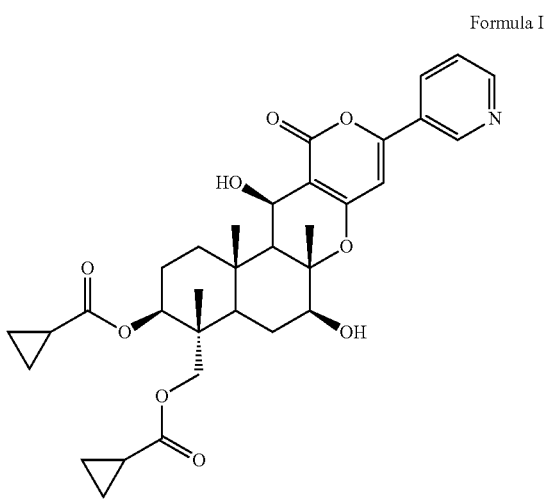

in which the fine particles contain the compound of formula I, at least one surfactant and water, which method comprises:

a) providing an aqueous slurry of coarse particles of the compound of the formula I, where the compound of the formula I is at least partially present in its crystalline form B, which, in an X-ray powder diffractogram at 25° C. and Cu-K$_\alpha$ radiation, shows at least three of the following reflexes, given as 2θ values: 8.0±0.2°, 9.5±0.2°, 10.7±0.2°, 11.0±0.2°, 11.2±0.2°, 11.7±0.2°, 14.2±0.2°, 15.6±0.2°, 16.5±0.2°, 17.7±0.2°, 21.5±0.2°;

b) comminuting the coarse particles in the slurry of the compound of formula I, which is at least partially present in its form B, in the presence of the at least one surfactant;

except for a formulation containing from 6 to 20 wt %, based on the total weight of the formulation, of at least one anionic polymeric surfactant having a plurality of $SO_3^-$ groups.

2. The method as claimed in claim 1, which comprises;

a1) suspending a solid form of the compound of formula I, which is different from said form B, in water to obtain an aqueous slurry of coarse particles of the compound of formula I;

a2) keeping the aqueous slurry of coarse particles of the compound of formula I for a time sufficient to achieve at least partial conversion of the compound of formula I into its form B;

a3) addition of at least one surfactant during steps a1) or a2) or after step a2), and b) comminuting the coarse particles in the slurry of the compound of formula I, which is at least partially present in its form B, after the addition of the at least one surfactant.

3. The method as claimed in claim 2, where the major amount of surfactant is added after completion of step a2.

4. The method as claimed in claim 2, where the aqueous slurry of the coarse particles of the compound of formula I is kept until at least 70% by weight of the compound of the formula I, based on the total amount of the compound of formula I in the suspension, are present in the form B.

5. The method as claimed in claim 2, where the at least partial conversion of the compound of formula I into its form B is achieved by keeping the aqueous slurry of the coarse particles of the compound of formula I for at least 0.5 h up to 8 days at a temperature in the range of from 25 to 95° C.

6. The method as claimed in claim 1, where step b) is performed to achieve a volume average diameter of the particles of not more than 8 μm.

7. The method as claimed in claim 1, where in the slurry the volume average diameter of the coarse particles is greater than 10 μm and up to 1000 μm.

8. The method as claimed in claim 1, where in the slurry at least 70% by weight of the compound of the formula I, based on the total amount of the compound of formula I, are present in the form B prior to comminution.

9. The method as claimed in claim 1, where in step b) comminution of the coarse particles is performed at a temperature of not more than 50° C.

10. The method as claimed in claim 1, where the concentration of the compound of formula I in the aqueous suspension during step b) is from 5 to 50% by weight, based on the total weight of the suspension.

11. The method as claimed in claim 1, where the concentration of the at least one surfactant in the aqueous suspension during step b) is from 1 to 30% by weight, based on the total weight of the aqueous suspension.

12. The method as claimed in claim 1, where the compound of the formula I has a purity of at least 97%.

13. The method as claimed in claim 1, where the surfactant comprises at least one anionic surfactant.

14. The method as claimed in claim 13, where the anionic surfactant comprises at least one anionic polymeric surfactant having a plurality of $SO_3^-$ groups.

15. The method as claimed in claim 13, where the anionic polymeric surfactant having a plurality of $SO_3^-$ groups is selected from the group consisting of salts of naphthalene sulfonic acid formaldehyde condensates, salts of alkylnaphthalene sulfonic acid formaldehyde condensates, and the salts of naphthalene sulfonic acid formaldehyde urea co-condensates.

16. The method as claimed in claim 13, where the surfactant further comprises at least one non-ionic surfactant.

17. The method as claimed in claim 16, where the non-ionic surfactant is selected from poly($C_2$-$C_4$)alkylenoxide polymers.

18. An aqueous suspension concentrate formulation of the compound of the formula I as defined in claim 1, wherein the compound of the formula I is at least partially present in its form Y, which, in an X-ray powder diffractogram at 25° C. and Cu-$K_\alpha$ radiation, shows at least three of the following reflexes, given as 2θ values: 9.7±0.2°, 10.3±0.2°, 11.3±0.2°, 14.0±0.2°, 15.5±0.2°, 16.4±0.2°, 17.6±0.2°.

19. The formulation of claim 18, which contains
    a) 1 to 30 wt %, based on the total weight of the formulation, of the pesticide compound of formula I, which is at least partially present in its form Y;
    b) 0.1 to 20 wt %, based on the total weight of the formulation, of at least one anionic surfactant,
    c) 0.1 to 20 wt %, based on the total weight of the formulation, of at least one non-ionic surfactant,
    d) 40 to 98.8 wt %, based on the total weight of the formulation, by weight of water.

20. The formulation of claim 18, where the volume average diameter of the pesticide particles is from 0.5 to 5 μm.

21. The formulation of claim 18, where the anionic surfactant comprises at least one anionic polymeric surfactant having a plurality of $SO_3^-$ groups.

22. The formulation of claim 21, where the anionic polymeric surfactant having a plurality of $SO_3^-$ groups is selected from the group consisting of salts of naphthalene sulfonic acid formaldehyde condensates, salts of alkylnaphthalene sulfonic acid formaldehyde condensates, and the salts of naphthalene sulfonic acid formaldehyde urea co-condensates.

23. The formulation of claim 18, where the non-ionic surfactant is selected from poly($C_2$-$C_4$)alkylenoxide polymers.

24. The formulation of claim 18, where the non-ionic surfactant is selected from poly(ethyleneoxide-co-propyleneoxide) polymers having a HLB in the range of 12-20.

25. A method for protecting plants from attack or infestation by insects, acarids or nematodes comprising contacting the plant, or the soil or water in which the plant is growing, with an aqueous pesticide formulation according to claim 18 in pesticidally effective amounts.

26. A method for controlling insects, arachnids or nematodes comprising contacting an insect, acarid or nematode or their food supply, habitat, breeding grounds or their locus with an aqueous pesticide formulation according to claim 18 in pesticidally effective amounts.

27. A method for protection of plant propagation material comprising contacting the plant propagation material with an aqueous pesticide formulation according to claim 18 in pesticidally effective amounts.

28. Seed treated with the composition according to claim 18.

29. The method as claimed in claim 6, where step b) is performed to achieve a volume average diameter of the particles in the range from 0.5 to 5 μm.

30. The method as claimed in claim 9, where in step b) comminution of the coarse particles is performed at a temperature in the range from 10 to 40° C.

31. The method as claimed in claim 10, where the concentration of the compound of formula I in the aqueous suspension during step b) is from 10 to 40% by weight, based on the total weight of the suspension.

32. The method as claimed in claim 11, where the concentration of the at least one surfactant in the aqueous suspension during step b) is from 2 to 20% by weight, based on the total weight of the aqueous suspension.

* * * * *